Dec. 4, 1956 F. A. MAHAN Plant Pat. 1,532

PECAN TREE AND NUT

Filed Nov. 29, 1955

INVENTOR.
Fred A. Mahan.

BY Joseph F. Padlon

ATTORNEY

United States Patent Office

Plant Pat. 1,532
Patented Dec. 4, 1956

1,532

PECAN TREE AND NUT

Fred A. Mahan, Monticello, Fla.

Application November 29, 1955, Serial No. 549,904

1 Claim. (Cl. 47—62)

My present invention relates to trees producing edible nuts and more particularly to a pecan tree and the nut produced therefrom.

The particular type of pecan nut which I have produced is a cross between a Mahan and a Stuart pecan, both unpatented varieties. The new variety of pecan nut according to my invention was asexually reproduced first by budding in July 1949, and was done at my nursery located about three miles south of Monticello, Florida. My new nut can be best described by comparison with its antecedents. Also, it has been produced in the Monticello area in Florida. One of said nuts forming my invention is illustrated in the accompanying drawing and a color photograph thereof.

Figure 1:
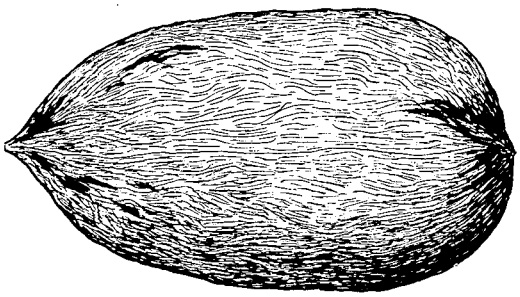
Fig. 1 is a side view of my new variety of pecan nut.
Figure 2:
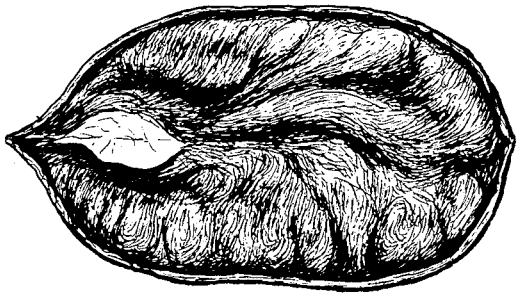
Fig. 2 is a longitudinal section thereof.
Figure 3:
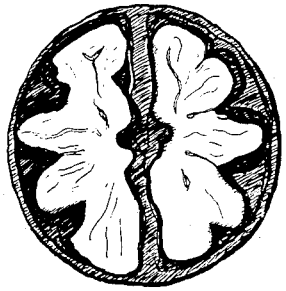
Fig. 3 is a cross section thereof.

The following constitutes a detailed description of the tree and fruit of my new variety of pecan.

The tree is vigorous and rapid in growth, moderately spreading, averaging about 90% as to height.

The leaves are large and rather pointed resembling the leaf of the Mahan tree.

The bark has prominent markings and in this respect resembles that of the Mahan variety.

The buds are rather sharply pointed at their apex.

The tree is more productive than the Stuart variety and begins to bear fruit earlier than the Stuart, making three to six nuts to the cluster. The tree is resistant to disease, and in this respect resembles the Stuart variety. The new pecan tree has not to date been susceptible to pecan scab which is usually prevalent on most pecan varieties in the Monticello area. By observation of the leaves and nuts the typical pecan scab lesions are not present on the new variety. The Moore, Schley, Success, Moneymaker, Mahan and other varieties have pecan scab in the Monticello area, while the Stuart variety does not.

The new variety is the result of controlled crossing between the Mahan and the Stuart varieties. Pistillate flowers were hand pollinated and covered. Nuts were planted from a number of such crosses. From one of the nuts the tree originated producing the new pecan. The instant variety is believed to be the largest pecan yet developed. All of the aforesaid mentioned varieties are unpatented. Furthermore, the tree is above average, over most varieties in productivity, producing a good crop yearly.

The blooms on the tree appear earlier in the season than the Stuart, and the nuts mature about ten days earlier in the fall than the Stuart variety, but later than the Mahan variety.

The nuts are heavier but not as long as the Mahan variety. The shell is heavier than the Mahan but thinner than the Stuart variety.

When picked at ripening time the nuts average between twenty-six to thirty per pound. However, when dried they will weigh slightly less.

The size of the nut averages two to two and one-quarter inches in length and is about 20/16 or 1¼" in diameter and about four inches round. The nut is ovate in shape having a pointed apex at one end and a plump rounded or spherical portion at the other end. When looking at the apical end of the nut, it will be noted that there are two depressions one on each side of the nut and meeting at the apical end.

The exterior of the shell is venated and somewhat striated forming depressions or sutures but smooth, having disparate blackened areas. The shell is of a medium brown coloring with black markings or areas prominent toward the apex of the nut. The nut can be readily cracked. The shell is medium thin as compared with the Mahan and Stuart varieties.

The flavor of the kernel or meat is good, and has a relatively high percentage of oil thus preventing much loss in weight of the nut on drying or standing. The kernel is better flavored than either the Stuart or Mahan variety and is fine grained and firm. Also, it is easily removed from the shell. The sutures extend evenly through the longitudinal axis of the shell but when the shell is opened separate readily from the kernel.

Having thus described and illustrated my invention herein I claim:

A new variety of pecan tree as herein disclosed and illustrated being cross bred from the Mahan and Stuart varieties, said tree being rapid in growth, vigorous, having leaves large and rather pointed, and having a bark with prominent markings and limbs which produce buds which are rather sharply pointed at their apex and whose blooms appear a week earlier than the Stuart and whose nuts mature about ten days earlier in the fall than the Stuart variety; and its nuts averaging about 1¼ inches in diameter and about four inches round and having a length of about two to two and one-quarter inches, the nuts being ovate shaped with a pointed apex at one end and a plump rounded portion at the other end, the kernel being better flavored than the Mahan or Stuart variety and having a moderately high percentage of oil, plump and relatively thick and easily separable from the shell, the shell thereof being of medium brown color, with black markings prominent at the apex end of the shell, said shell being medium thin with striations running longitudinally of the nut.

No references cited.